United States Patent [19]

Divjak

[11] Patent Number: 5,520,539
[45] Date of Patent: May 28, 1996

[54] DENTAL IMPRESSION TRAY FOR OPTIONAL PARTIALLY TOOTHLESS JAW AND TOOTHLESS JAW WITH IMPLANTS

[75] Inventor: Milan Divjak, Celje, Slovenia

[73] Assignee: Chris Company, Inc., Ridgewood, N.J.

[21] Appl. No.: 318,128

[22] Filed: Oct. 5, 1994

[30] Foreign Application Priority Data

Feb. 25, 1994 [SI] Slovenia .................. P-9400102

[51] Int. Cl.$^6$ ........................................ A61C 9/00
[52] U.S. Cl. ............................... 433/37; 433/38
[58] Field of Search ................... 433/37, 38, 41, 433/42, 45, 47

[56] References Cited

U.S. PATENT DOCUMENTS 4,375,965  3/1983  Weissman .................. 433/37
5,127,829  7/1992  Nordquist .................. 433/37
5,213,498  5/1993  Pelerin .................... 433/37

Primary Examiner—Stephen Funk
Attorney, Agent, or Firm—Richard M. Goldberg

[57] ABSTRACT

The dental impression tray for optional partially toothless jaw and toothless jaw with implants consists of a basic impression tray (1) and of a paired impression tray (2) freely arrangeable and positioned upon it, whereat the tray (1) is executed basically as a grooved horseshoe-shaped profile (3), whose side edges (4) are thickened with the purpose of strengthening, and the paired impression tray (2) is executed as a stiff horseshoe-shaped U-profile, which rests exactly on the outer thick edge (4) of the tray (1) so that between the trays (1) and (2) a space (6) is formed, which can accept a tooth with the impression material, and the thin-walled profile (3) of the tray (1) is foreseen for making holes (7) by handy dental tools at optional places in accordance with the state of the treated jaw.

2 Claims, 1 Drawing Sheet

DENTAL IMPRESSION TRAY FOR OPTIONAL PARTIALLY TOOTHLESS JAW AND TOOTHLESS JAW WITH IMPLANTS

BACKGROUND OF THE INVENTION

The invention relates to a dental impression tray for an optional partially toothless jaw and for a toothless jaw with implants on optional places, which is used for taking and producing impressions for dentures.

The technical problem to be solved by the present invention is how to make an impression tray that will make possible and ensure doctrinally correct impressions of toothless jaw sections as well as of jaw sections with teeth optionally arranged thereon, thereby excluding the possibility of breaking the impressed remaining teeth or implants on the intermediate mold due to the negative angles between the impression material and the cast model.

There is known an impression tray for partially toothless jaw and toothless jaw with implants, which is basically executed as a horseshoe-shaped U-profile.

A drawback of this tray at the application on a partially toothless jaw lies in the fact that a larger quantity of the impression material than really needed must be used in the groove in the area of the toothless jaw section. This represents an unnecessary cost. A further disadvantage is the fact that such increased quantity of impression material excludes the application of some kinds of impression materials.

Since at the process of impression production the toothless jaw section reacts (deforms) differently from the jaw section with hard tissue, an impression is received, which does not represent the real supporting surface for the denture.

If this impression tray is used at the production of the impression of a partially toothless jaw, it is rather likely that at taking off (shelling off) the intermediate mold will break in the area of teeth or implants because of negative angles thereon. In such case the intermediate mold has to be repaired, whereat errors can occur. Any corrections represent additional work and cost.

A further known impression tray for partially toothless jaw and toothless jaw with implants consists of an impression tray for toothless jaw, to which at a previously defined place or places a supplement is added for the jaw section with teeth or implants.

Thus the above-mentioned drawback is partially eliminated. This impression tray at toothless sections rests correctly on the alveolar ridge and at sections with teeth its excavated hollow makes possible an appropriate impression.

An essential drawback of this impression tray is that it is only applicable at single defined arrangements of teeth or implants in the jaw. Such trays are only produced for the most frequent arrangements of teeth, i.e. for upper and lower front teeth.

Since there exist many atypical arrangements of teeth and implants in the jaw, it is obviously impossible to produce trays for all possible cases on an industrial scale and at an adequate price. Nor is it sensible for a dentist to possess such a number of different trays as they tie up too much money, occupy too much room and, last but not least, are not fully suitable.

Furthermore it is known that some impression materials are specially suited for a good impression of the toothless jaw and other impression materials for the impression of hard tissues making possible the taking off of the intermediate mold of the impression section also in an area with negative angles.

In view of the above-described different characteristics of the impression materials for the toothless jaw and the jaw with hard tissue, at the application of this impression tray the exclusive nature of the chosen impression material shows as a good impression on toothless jaw section or as later undamaged taking off the intermediate mold of the impression section, respectively.

Therefore there appears a need, though in a relatively small number of teeth states, for the application of two different impression materials, i.e. the material for the toothless jaw and the material for hard tissues.

Known impression trays do not make possible such application.

SUMMARY OF THE INVENTION

According to the present invention, the described technical problem is solved by a two-part impression tray. The basic impression tray, whose shape is equal to the shape of the impression tray for toothless jaw, is executed as a thin-walled horseshoe-shaped groove to accept the impression materials. In order to achieve the required stiffness of the groove, its both free edges are strengthened by a bulge of an approximately circular cross-section and also reinforced if necessary, which depends on the chosen materials. Also by its shape, the thick edge is adapted for resting on the functional edge.

On the convex side of the groove of the impression tray, the second part of the impression tray is freely arranged. This part is also formed as a horseshoe-shaped groove with a nearly rectangular cross-section. The second part rests exactly on the strengthened thick outer edges of the basic tray so that between both parts an empty space appears, which is large enough to accept the teeth and the impression material.

The thin-walled part of the basic tray is made of such material that the dentist can perforate it in the teeth sections of an individually treated jaw by standard dental tools such as drills, grinding stones, knives etc.

The thus prepared impression tray according to the invention makes possible the production of the impression in one or two steps and using one or two different impression materials.

First the impression of the toothless jaw section is taken by using the basic tray and impression materials for the toothless jaw, whereat the functional movements are relieved for the volume of the upper impression tray not yet arranged.

Then the upper impression tray is inserted and the impression of the hard tissues is taken by using the second impression material suited for hard tissues.

The quality of the impression made by such two-part impression tray certainly compensates for its price though the basic impression tray cannot be used many times but as a rule only once and several times at similar teeth states.

BRIEF DESCRIPTION OF THE DRAWINGS

The impression tray according to the invention is explained in more detail on the basis of an example of embodiment and of a drawing, in which.

DESCRIPTION OF THE PREFERRED EMBODIMENT

Figure 1:
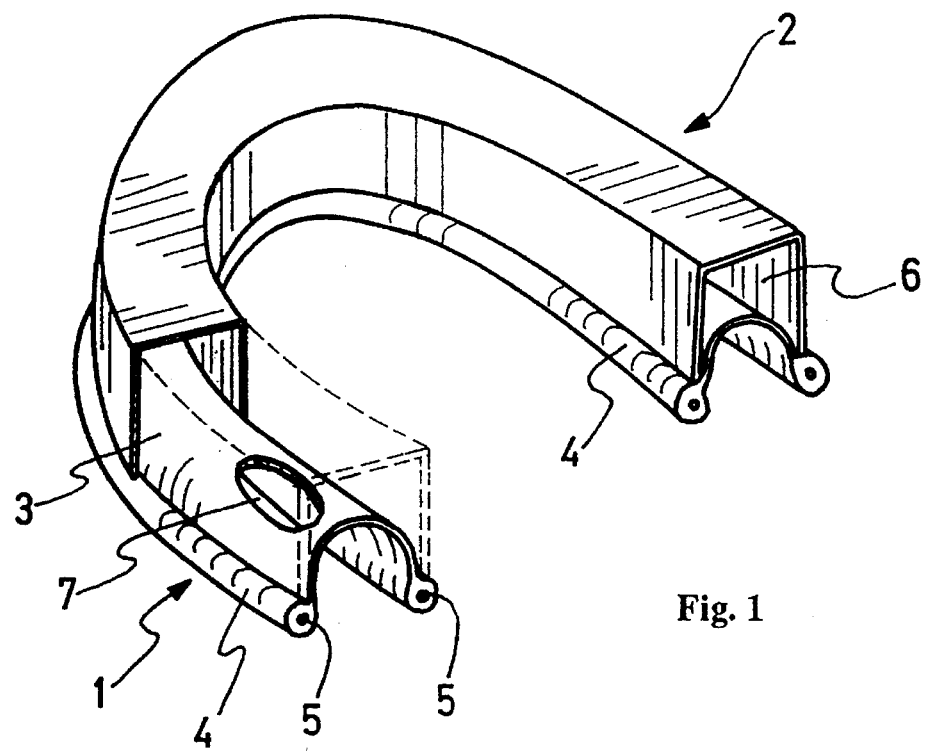
FIG. 1 is a perspective view and partial cross-section view of the invention.
Figure 2:
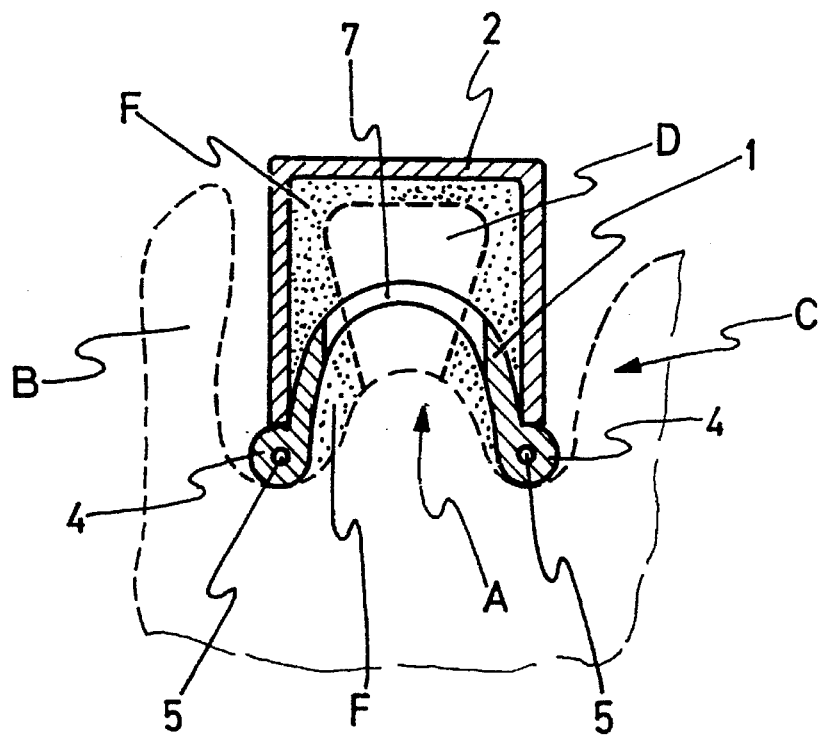
FIG. 2 is a cross-section of the invention and is arranged on a jaw section with a tooth.

The dental impression tray for optional partially toothless jaw and toothless jaw with implants consists of a basic impression tray 1 and of a paired impression tray 2 that is freely arrangeable and positioned upon the former. The tray 1 is basically executed as a grooved horseshoe-shaped profile 3, whose side edges 4 are thickened for the purpose of strengthening and, if necessary, reinforced with a strengthening insert 5 so as to achieve the required stiffness.

The paired impression tray 2 is realized as a stiff horseshoe-shaped U-profile, which exactly rests on the outer thick edge 4 of the tray 1 so that between the trays 1 and 2 a space 6 is formed, which can accept a tooth with the impression material. The described impression tray 2 can also be realized as a segment of the horseshoe-shaped U-profile.

The thin-walled profile 3 of the tray 21 is made of a material that makes possible the cutting of holes 7 by handy dental tools at optional places in accordance with the state of the treated jaw.

The impression tray 1 is placed on the jaw A so that it with its edges 4 rests exactly on the passage between the jaw A and the lip B or the tongue C. Through holes 7 the teeth D project. On the impression tray 1 the impression tray 2 is placed so that it rests on the edges 4 and freely surrounds the teeth D in its space 6. The space 6 and the space on the concave side of the tray 1, which is closed by the jaw A, are filled by the impression material F, which makes the required shape of the impression.

It is evident that the described impression tray according to the invention is dimensionally fitted to the dimensions of the jaws. In industrial production it should be produced in several sizes as it is the case with known impression trays.

The materials are chosen in accordance with technological requirements, especially concerning the stiffness of both trays and the possibility of making holes in the basic tray in dental surgery by handy dental tools. In any case materials must also correspond to the hygienic requirements.

The treatment of both impression trays to achieve good grasping of the impression materials by perforation, ridges and similar is performed by known methods.

I claim:

1. Dental impression tray for a partially toothless jaw or a toothless jaw with implants, comprising:

a first basic impression tray (1), and a second impression tray (2) freely arrangeable and positioned upon the basic impression tray (1), whereat:

the basic impression tray (1) has a thin wall (3) with an overall horseshoe shape and an inverted U-shaped cross-section which together define a horseshoe shaped groove, said thin wall having spaced apart lower thickened side edges (4), the second impression tray (2) has a stiff overall horseshoe-shape and an inverted U-shaped cross-section, the second impression tray (2) resting exactly on an outer side of the thickened side edges (4) of the basic impression tray (1) so that between the trays (1, 2) a sufficient space (6) is formed for accepting a tooth with impression material, and the thin wall (3) of the basic impression tray (1) is sufficiently thin to permit a dentist to cut individual holes (7) at desired places in accordance with the state of the treated jaw.

2. Dental impression tray according to claim 1, wherein the thickened side edges (4) of the basic impression tray (1) are reinforced by a strengthening insert (5) therein.

* * * * *